United States Patent
Sharma et al.

(10) Patent No.: US 11,398,304 B2
(45) Date of Patent: Jul. 26, 2022

(54) IMAGING AND REPORTING COMBINATION IN MEDICAL IMAGING

(71) Applicant: Siemens Healthcare GmbH, Erlangen (DE)

(72) Inventors: Puneet Sharma, Princeton Junction, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 225 days.

(21) Appl. No.: 15/961,047

(22) Filed: Apr. 24, 2018

(65) Prior Publication Data

US 2019/0326007 A1 Oct. 24, 2019

(51) Int. Cl.
*G16H 30/40* (2018.01)
*G16H 15/00* (2018.01)
*G16H 80/00* (2018.01)
*G16H 30/20* (2018.01)
*G16H 10/60* (2018.01)

(52) U.S. Cl.
CPC ............ *G16H 30/40* (2018.01); *G16H 15/00* (2018.01); *G16H 80/00* (2018.01); *G16H 10/60* (2018.01); *G16H 30/20* (2018.01)

(58) Field of Classification Search
CPC ........ G16H 30/20; G16H 40/20; G16H 40/67; G16H 80/00; G16H 10/60; G16H 15/00
USPC .......................................................... 705/2
See application file for complete search history.

(56) References Cited

U.S. PATENT DOCUMENTS

| | | | |
|---|---|---|---|
| 2005/0065423 A1* | 3/2005 | Owen | G06F 19/00 600/407 |
| 2005/0121505 A1* | 6/2005 | Metz | G16H 10/65 235/375 |
| 2005/0203868 A1* | 9/2005 | Judd | G16H 40/67 |
| 2007/0118399 A1* | 5/2007 | Avinash | G16H 10/60 705/2 |

(Continued)

FOREIGN PATENT DOCUMENTS

WO  WO-2013075127 A1 * 5/2013 ......... G06F 16/5838

OTHER PUBLICATIONS

Wardlaw, J M; Davies;Acting on incidental findings in research imaging; BMJ : British Medical Journal (Online) 351 BMJ Publishing Group LTD. (Nov. 10, 2015) (Year: 2015).*

(Continued)

*Primary Examiner* — Hiep V Nguyen

(57) ABSTRACT

Since the final output for medical imaging is the radiology report, the quality of which is largely dependent on the radiologist, there is a need for a comprehensive system for both medical imaging and reporting. Imaging and radiology reporting are combined. Image acquisition, reading of the images, and reporting are linked, allowing feedback of readings to control acquisition so that the final reporting is more comprehensive. Clinical findings typically associated with reporting may be used automatically to feedback for further or continuing acquisition without requiring a radiologist. A clinical identification may be used to determine what image processing to perform for reading, and/or raw (i.e., non-reconstructed) scan data from the imaging system are provided for integrated image processing with report generation.

19 Claims, 3 Drawing Sheets

(56) References Cited

U.S. PATENT DOCUMENTS

| | | | |
|---|---|---|---|
| 2008/0119717 A1* | 5/2008 | Profio | G16H 40/20 600/407 |
| 2009/0022386 A1* | 1/2009 | Karau | A61B 6/032 382/131 |
| 2012/0020536 A1* | 1/2012 | Moehrle | G06T 7/74 382/128 |
| 2012/0035963 A1 | 2/2012 | Qian et al. | |
| 2013/0083978 A1* | 4/2013 | Frederick | G16H 50/70 382/128 |
| 2013/0311472 A1* | 11/2013 | Cohen-Solal | G06F 16/285 707/737 |
| 2016/0350919 A1 | 12/2016 | Steigauf et al. | |
| 2017/0076043 A1* | 3/2017 | Dormer | G16H 30/20 |
| 2017/0337329 A1 | 11/2017 | Liu et al. | |

OTHER PUBLICATIONS

U.S. Appl. No. 15/957,143, filed Apr. 19, 2018.
European Search Report dated Jan. 23, 2020 in corresponding European Patent Application No. 19168042.0.

* cited by examiner

IMAGING AND REPORTING COMBINATION IN MEDICAL IMAGING

BACKGROUND

The present embodiments relate to medical imaging and reporting from the imaging. Medical reports, such as a radiology report, are primarily a written communication between radiologists, medical professionals, and patients. The reports often contain complex anatomical, technical, and medical information with images, values for measurements and textual notations providing an analysis or summary of pathologies represented in the images (e.g., key findings). The comprehensive explanation has significant value in disease diagnosis, prognosis, and treatment.

The process of image acquisition and image reporting are currently decoupled. The role of the medical imaging scanner is primarily to produce high quality diagnostic images, while the radiologist's role is to interpret those images and produce the radiology report with the key findings. Due to focus on value-based care and increased productivity, there is more emphasis on quantifying and improving the "value" of the overall imaging exam. In recent years, there has been a lot of development on the image acquisition side to standardize image protocols to achieve consistent high-quality images across multiple clinical sites. This focus does not deal with inefficiencies in reporting or inconsistency in reporting.

SUMMARY

By way of introduction, the preferred embodiments described below include methods, systems, instructions, and computer readable media for combined imaging and reporting. Since the final output is the radiology report, the quality of which is largely dependent on the radiologist, there is a greater need for a comprehensive system for both medical imaging and reporting. Imaging and radiology reporting are combined. Image acquisition, reading of the images, and reporting are linked, allowing feedback of readings to control acquisition so that the final reporting is more comprehensive. Clinical findings typically associated with reporting may be used automatically to feedback for further or continuing acquisition without requiring a radiologist. A clinical identification may be used to determine what image processing to perform for reading, and/or raw (i.e., non-reconstructed) scan data from the imaging system are provided for integrated image processing with report generation.

In a first aspect, a method is provided for imaging and generating a radiology report in a medical system. A medical imaging scanner scans a patient. An image processor receives a clinical identification for the patient. Image processing is selected based on the clinical identification. The image processor image processes first scan data from the scanning based on the selected image processing. Information is fed back to the medical imaging scanner based on the imaging processing. The medical imaging scanner rescans based on the feedback information. The image processor generates the radiology report in response to the first scan data, the feedback information, and/or second scan data from the rescanning. The radiology report has narrative text characterizing the patient and is output.

In a second aspect, a system is provided for imaging and generating a radiology report. A medical imager is configured to scan a patient. The configuration being for a clinical application. A processor is configured to receive scan data from the medical imager, apply image processing to the scan data, determine a clinical finding from the image processing, control the medical imager based on the clinical finding, and generate the radiology report from the clinical finding. An interface is configured to output the radiology report.

In a third aspect, a method is provided for imaging and generating a radiology report in a medical system. First and second scan data are received from first and second medical scanners. The first and second scan data represent first and second patients and are without reconstruction into a three-dimensional object space. First and second clinical indication tags are obtained for the first and second scan data. Image processing, including reconstruction, of the first and second scan data is performed. The image processing of the first scan data is different than of the second scan data based on the first and second clinical indication tags being different. First and second radiology reports are generated from information provided by the image processing. The first and second radiology reports are output. Due to the linking of acquisition and reading in generating a report, the report may be generated without display of any images from the first and second scan data to a human after receiving and through the image processing and the generating.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
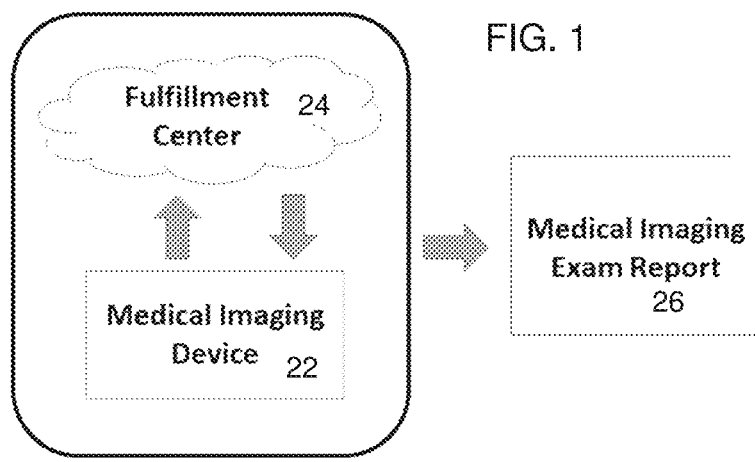
FIG. 1 is one embodiment of a system for imaging and generating a medical imaging examination report.

A comprehensive medical imaging and reporting device or process scans subjects and produces clinical reports as final output. As shown in FIG. 1, the comprehensive medical imaging and reporting device includes a medical imaging device 22 and a fulfillment center or processor 24 for interacting to generate the medical imaging examination report 26. In contrast to the typical medical imaging scanners, which produce medical images as their end product, the comprehensive device produces the medical imaging exam report describing the main findings in the patient's imaging exam. The fulfillment center 24 is a medical image reading and reporting infrastructure. Unlike teleradiology operations, that are independent of imaging, the fulfillment center 24 is specifically configured to operate in an intrinsically interconnected manner with the medical imaging device 22. Feedback may be used to control imaging based on on-going clinical findings from the imaging. Feed forward may be used for reconstruction by the fulfillment center 24 rather than the medical imaging device 22, allowing for clinical finding-based reconstruction. Clinical identification from the medical imaging device 22 may be used by the fulfillment center 24 to select image processing as the iterative or interactive imaging and report reading continues.

Figure 2:
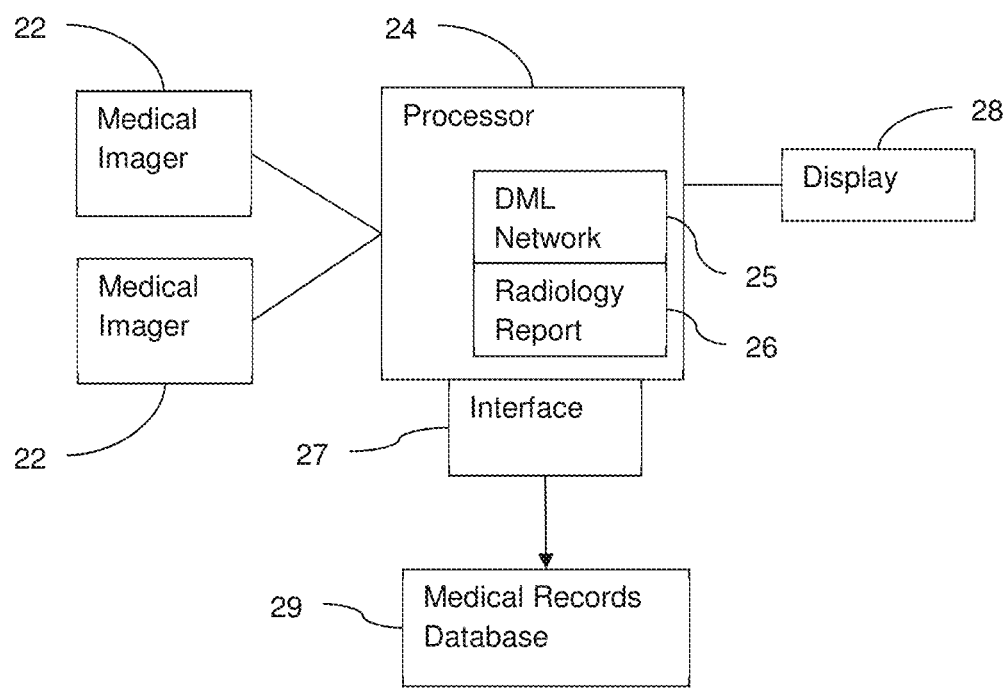
FIG. 2 is another embodiment of a system for imaging and generating a medical radiology report.

FIG. 2 shows a block diagram of one embodiment of a system for imaging a patient and generating of a radiology report. The system provides for linked imaging, reading, and reporting. Due to the intrinsically interconnected arrangement between imaging and reading, (1) feedback may be used to control imaging due to clinical findings, (2) clinical identification may be provided with scan data for reading based on the clinical identification rather than mere performance of radiology reading based on an image, and/or (3) non-reconstructed data may be provided for reconstruction based on the reading rather than reading from images with no control over the reconstruction used. In one embodiment, the system implements the method of FIG. 4 and/or the arrangement of FIG. 3.

The system includes one or more medical imagers 22 and the fulfillment center, shown as a processor 24. Other parts of the system include an interface 27, a medical records database 29, and a display 28. Additional, different, or fewer components may be provided. For example, a user interface or input device is provided on the medical imager 22 and/or for the processor 24. In another example, a network or network connection is provided, such as for networking different components (e.g., medical imagers 22 with the processor 24 and/or the processor 24 with the database 29).

The interface 27, processor 24, and/or display 28 are part of a server, workstation, or computer. In one embodiment, the interface 27, processor 24, and/or display 28 are a server or workstation. The medical records database 29 is part of a separate computer from the processor 24, such as being in a cloud hosted electronic health record or electronic medical records system.

The medical imagers 22 and the processor 24 are at different facilities, such as being remote from each other. The medical imagers 22 and processor 24 are in different buildings, cities, states, or countries. For example, the processor 24 connects to the multiple medical imagers 22 through a high-speed computer network, so is a server or operates in the cloud. In alternative embodiments, the processor 24 (i.e., fulfillment center) may be located on premise with the medical imagers 22, such as in a same building or facility, but in a different room. In yet other alternative embodiments, the processor 24 is part of or in a same housing with the medical imager 22. Each medical imager 22 includes a separate processor 24 or one medical imager 22 implements the processor 24 for use by that imager 22 and other imagers 22.

Where the interconnection between the imager 22 and the processor 24 is broken, the imager 22 may continue to function. Scan data (e.g., images) may be processed into visually interpretable images and routed to a picture and archiving system for later reading and/or report generation. This hybrid operates according to a traditional system of generating an image, reading the image, and reporting without the interconnection and communications for linked imaging, reading, and reporting.

The medical imager 22 is a magnetic resonance (MR), computed tomography (CT), x-ray, ultrasound, or nuclear medicine (e.g., positron emission tomography or single photon computed tomography) scanner. In other embodiments, the medical imager 22 is a multi-modality device, such as a combination of nuclear medicine and x-ray or CT. In yet other embodiments, invasive, other non-invasive, or minimally invasive imaging systems are used.

The medical imager 22 is configured to scan a patient. The same imager 22 may be used to scan different patients at different times. Other imagers 22 may be used to scan other patients.

To scan a patient, the medical imager 22 is configured by settings or values for scan parameters. The same imager 22 may operate differently based on the settings. For example, the voltage, collimator settings, pulse settings, offsets, spatial position, speed, travel path, pulse sequence, timing, coil to be used, amplitude, focus, and/or other parameters control the physics for scanning a patient. Different modalities have different parameters for scanning. Other parameters control subsequent processing of the acquired data, such as filtering, amplifying, reconstructing, and/or detecting.

Different settings are used for different clinical applications. For example, a field of view and/or focal location is different for a chest scan than for a lower torso or whole-body scan. Different settings are used for the parameters of a same modality for different applications. The application may be a type of scanning by region and/or by pathology (e.g., checking for a particular disease). The technician configures the medical imager 22 for a given patient based on a referring physicians indication or selection of the clinical application. The configuration may use a drop down or other menu structure allowing selection of the clinical application and/or adjustment or entering of one more settings.

In some cases, a generic clinical application is selected. For example, a patient complains of chest pain. A cardiac imaging application is selected. Later findings may be that there is a blockage of an artery, so a more specific clinical application for vessel imaging may be used later. Alternatively, the more specific clinical application is prescribed initially without having the imaging-based findings confirm the expected disease, location, or severity.

For use with a linked reading and reporting, the medical imager 22 is configured to output a clinical identification or indication tag to the processor 24. The clinical identification tag may be the clinical application or indication of the clinical application (e.g., settings used for scanning). In other embodiments, the clinical identification tag is a symptom, measurement from the patient, or other patient information indicating a reason for the imaging. The medical imager 22 communicates the clinical identification tag to the processor 24 for use in automatically generating findings for the patient.

The medical imager 22 is configured to output scan data to the processor 24. The scan data is data resulting from the scan at any stage of processing. For example, data without reconstruction is provided. For CT, the data may be detector measurements for a plurality of projections without reconstruction into values for specific spatial locations. For MR, the data may be k-space data prior to Fourier transform to determine values for specific spatial locations. For nuclear imaging, the data may be line-of-response values prior to tomography to assign specific spatial locations. As another example, data after reconstruction is provided. Filtering, detection, scan conversion, and/or other image processing may or may not be applied to the data for communication to the processor 24. The medical imager 22 provides image data (e.g., scan data) as data resulting from scanning with any amount of processing towards generating an image. The image data may be formatted for display, such as RGB values, or may be in a scan format (e.g., scalar values).

The processor 24 of the fulfillment center is a general processor, control processor, digital signal processor, application specific integrated circuit, field programmable gate array, or other hardware processor for image processing. The processor 24 is part of a computer, workstation, server, or other device configured to apply image processing, derive findings specific to patient, and/or to generate a radiology report 26. The processor 24 may be a network of computing devices, such as multiple computers or servers. The processor 24 is configured by software, hardware, and/or firmware.

The processor 24 is configured to interrelate with the medical imager or imagers 22. The processor 24 is a second sub-unit of the comprehensive device for imaging and report generation. Raw and/or processed medical imaging data (e.g., scan data) is received to produce as output the clinical report 26. Other information may also be received, such as the clinical indication tag and/or patient information.

The processor 24 is configured to apply image processing to the scan data. Any type of image processing may be performed. For example, reconstruction, quality assurance of the scan, filtering, denoising, detection, segmentation, classification, quantification, and/or prediction are applied. The image processing provides quality of imaging, measurements or quantification for the patient, image data more responsive to or indicative of given conditions, location information, size information, type information, recommended clinical decisions, expected outcome or progression, and/or other information that may be used for reading and reporting. Natural language processing may be implemented for generating natural text for the radiology report 26 from the image processing results and/or scan data.

The image processing uses hand coded processing (e.g. algorithm) and/or application of one or more machine-learned networks. The fulfillment center implemented by the processor 24 may be either fully automatic or semi-automatic, assisted by artificial intelligence (AI) algorithms for the various image processing tasks such as quality assurance of the imaging exam, reconstruction, filtering and denoising, detection, segmentation, classification, quantification, prediction, natural language processing, etc.

Figure 3:
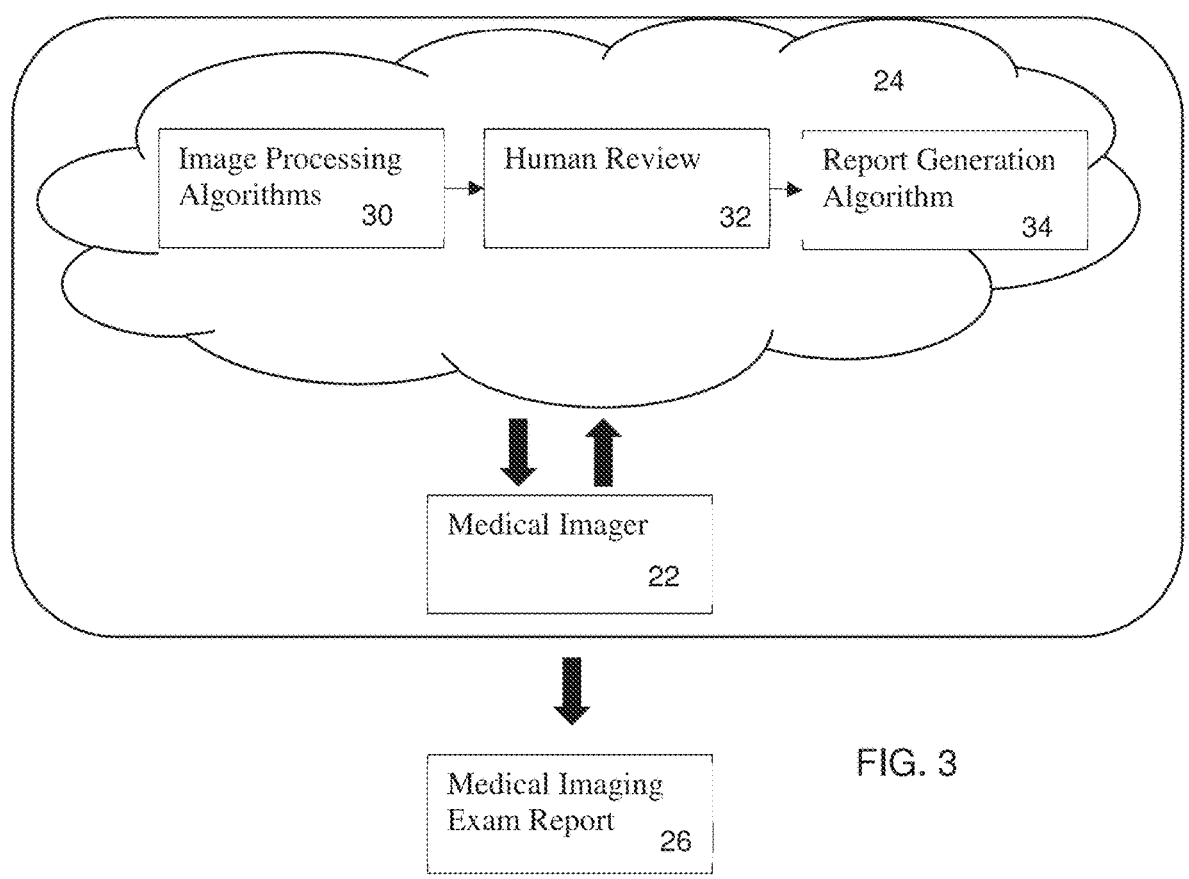
FIG. 3 illustrates an example interaction for generation of a medical imaging examination report.

FIG. 3 shows an example semi-automatic approach or arrangement. The processor 24 applies automatic image processing algorithms or machine-learned networks 30. The output of the image processing is reviewed 32 by a human, such as a radiologist, for consistency, accuracy, and/or errors. A report generation algorithm 34 is then applied to generate the radiology report 26. Humans might be in the loop at the fulfillment center for quality assurance of all or a subset of findings and/or the report. In alternative embodiments, the human review 32 is not provided, other than a radiologist, patient, or referring physician reviewing the final radiology report 26. Fully automatic report generation is provided based on interaction between the imager 22 and the processor 24.

The image processing 30, report generation 34, and/or other processes implemented by the processor 24 use the intrinsic interconnection with the medical imager 22. The processor 24 is configured to select the image processing to apply based on the interconnection. The clinical application tag indicates the type of examination being performed and/or the reason for the examination (e.g., symptom). A specific set of image processes may be automatically invoked at the fulfillment center based on the clinical indication tag. A look-up table is used. Alternatively, a machine-learned network (e.g., deep machine-learned network 25) is trained to select image processes and/or settings for image processing based on the clinical indication tag, scan data, patient information, and/or other information from the imager 22 and/or other sources. The clinical indication tag is used to classify and route the examination for the patient. The image processing to be performed depends on the type of exam being performed on the specific medical imaging device, as indicated by the clinical indication tag. For example, the clinical indication tag includes the symptom of chest pain and/or a cardiac imaging application with an ultrasound scan. Image processing for this symptom and/or application are selected, such as image processing for detection of stenosis, faulting valve operation, and/or abnormal heart wall motion.

In other embodiments, the clinical indication tag is not used. The scan data is image processed to determine the image processing to perform, such as applying a machine-learned network (e.g., deep machine-learned network 25) to the scan data and/or header information with a frame of imaging data to select image processing.

The intrinsic interconnection may be used in another way. In a typical use, the medical imager 22 performs reconstruction based on the selected settings for imaging, such as setting selected for the particular application or type of scan with or without consideration of patient characteristics. Given the interconnection, the raw scan data or scan data prior to reconstruction is provided to the processor 24 by the medical imager 22. The processor 24 is configured to reconstruct as part of the application of the image processing. The type of reconstruction or reconstruction settings to be used may be based on a look-up table from the clinical indication tag, clinical finding, and/or other information. Alternatively, a machine-learned network (e.g., deep machine-learned network 25) relates input data to output the reconstruction settings or type of reconstruction. The image processing algorithm at the fulfillment center may directly operate on the raw data or scan data prior to reconstruction and/or may reconstruct. No medical images are shown at the or by the medical imager 22 at this point. Clinical findings based on image processing occur prior to any human visualization of images from the scan data.

The processor 24 is configured to determine clinical findings. As part of report generation or image processing, clinical findings are found. The clinical finding is a medical opinion combining segmentation, detection, and/or classification. The clinical finding provides a severity, location, relationship to a symptom, and/or type of pathology or disease. For example, a clinical finding is a detected and classified calcified atherosclerotic plaque causing moderate stenosis of the midportion.

The clinical finding is based on a look-up table and/or a machine-learned network. The results from image processing, patient information, clinical indication tag, and/or scan data are used to make one or more clinical findings. For example, a natural language processing system based on one or more machine-learned networks for text generation are used to provide the clinical finding. The clinical finding may be used to guide other image processing, report generation, and/or rescanning.

Another use of the intrinsic interconnection may be control of the medical imager 22 based on the clinical finding and/or results from image processing. By applying a machine-learned network (e.g., the deep machine-learned neural network 25) and/or a manually programmed algorithm, the processor 24 is configured to relate the input information (e.g., scan data, results of other image processing such as quantities, clinical finding, and/or patient data) to an output (e.g., scan settings, a type of scan, and/or a need for a rescan). The processor 24 outputs feedback in the form of settings for scan or image processing parameters to the medical imager 22. The settings are to redo a scan, alter a current on-going scan, and/or to perform a different scan. For example, the clinical finding is based on a generic cardiac scan. Based on the clinical finding, a further scan using contrast agents or different settings to focus on a vessel or pathology is to be performed. In alternative embodiments, the control is less direct. For example, the feedback is a request to perform a further scan or change some aspect of the scanning. The technician at the medical imager 22 implements the request.

In one example, the image processing applied is a quality check. The scan data is applied to a machine-learned network, which is trained to output an indication of quality. Based on the clinical indication tag, the quality check (e.g., the algorithm and/or network) is selected or tuned to check quality for the type of imaging. Where there is sufficient contrast, sufficient resolution, sufficient signal-to-noise ratio, limited artifacts, and/or other indication of quality, the scan data may be used for further image processing and/or clinical findings. Where the scan data is of insufficient quality, such as based on a threshold measure, the processor 24 uses the available information to provide settings for another scan. Other image processing may indicate a need or desire for different or additional scan data, such as imaging over additional heart cycles to better sample.

The processor 24 is configured to generate the radiology report from results of the image processing. The radiology report includes one or more clinical findings. Quantification, segmentation, detection, and/or other image processing results may also be included. A table of measurements, an image, patient information, the clinical indication tag, recommended actions, possible treatments, and/or other information may be included. Where rescanning is performed, the results from the different scans and/or image processing may be provided. Alternatively, the radiology report is generated from scan data and image processing for a last or most specific scan.

The generated radiology report may include free or narrative text. More structure may be provided, such as narrative text in a section communicating clinical findings with other sections being structured to include other information. In alternative embodiments, the radiology report is a structured report without narrative text, such as providing the clinical finding as a table of symptom, detected and classified disease, classified severity, and/or segmented or detected location.

In one embodiment, the processor 24 is configured to generate the clinical finding and/or radiology report with a machine-learned neural network. A natural language processing system is applied. The processor 24 applies the machine-learned network 25 and/or other natural language processing. The machine-learned network 25, as implemented by the processor 24, contributes to generating text for the clinical finding and/or radiology report. The processor 24 is configured to use the network 25 trained from a corpus of radiology terms and/or reports, plain language corpus, and/or one or more linguistic models of word embeddings to generate based on input scan data, image processing results, and/or measurements.

The natural language processing system includes a deep machine-learned network. Other natural language processing tools may also be included. Computational linguistics (e.g., linguist rules), information retrieval, and/or knowledge representation may be part of the natural language processing system.

The deep machine-learned network contributes to any part of the natural language processing system, such as analyzing, parsing, extracting, retrieving evidence, and/or generating a clinical finding. One network may be trained to perform all these acts. A separate network may be trained for each of the acts. Some acts may not use any machine-learned network. The deep machine-learned network is any now known or later developed neural network. In general, deep learning uses a neural network with raw data or data without conversion to other features as input and a ground truth. The relationship of the values of the input raw data to the ground truth is learned. Deep learning may be used without including specific linguistic rules. A deep neural network processes the input via multiple layers of feature extraction to produce features used to output. The deep learning provides the features used to generate the output. In alternative embodiments, other machine learning is used, such as a Bayesian network, probabilistic boosting tree, or support vector machine.

For natural language processing, the deep-machine learned network may be a recursive neural network, a convolutional network, an attention model, and/or a long term-short memory network. Any architecture may be used. Other deep learned, sparse auto-encoding models may be trained and applied. The machine training is unsupervised in learning the features to use and how to classify given an input sample (i.e., feature vector). The combination of information in the raw data indicative of the ground truth is learned, and an output given input combination of information is learned.

The trained network is stored in a memory. The trained artificial intelligence (i.e., machine-learned network) is stored. The result of the training is a matrix or other model. The model represents the learned knowledge through machine training using deep learning. Other machine-learned network representations may be used, such as a heirarchy of matrices or other non-linear models.

Once trained, the machine-learned network is applied by a machine, such as a computer, processor, or server. The machine uses input data for a patient (i.e., scan data, clinical indication tag, results from image processing, patient information, and/or information derived therefrom) and the machine-learned network to generate an output, such as a clinical finding or the radiology report 26 with the clinical finding.

Other information may be generated for inclusion in the radiology report or for other outputs. For example, reimbursement codes are automatically generated. A look-up table based on clinical indication tag, scan data, patient information, and/or other information provides the codes. Alternatively, a network is trained by machine learning to provide the codes.

The processor 24 may create multiple reports for the same examination of the same patient for different end consumers: referrer, patient, and radiologist. The machine-learned network is trained to output different narrative text, report content, report structure, and/or other radiology report information for different end users or viewers.

In another embodiment, the processor 24 is configured to identify similar cases and/or provide statistical information. The processor 24 uses clinical findings, image processing results (e.g., quantification), patient information, and/or other information to identify medical records for patients that are similar. The identified medical records are used to calculate statistical similarities and/or differences. The statistical information and/or listing of similar patients may be output separately from the report 26 or included in the report 26.

In another embodiment, the processor 24 is configured to prioritize determining clinical findings and/or generating a report. Since the processor 24 may communicate with multiple different medical imagers 22, a priority between imagers 22 is provided. Even for one imager 22, a priority between patients may be provided. The order of receipt may be used. Using priority determined based on manual programming or application of a machine-learned network, a clinical finding or radiology report 26 may be generated for one patient before another patient even though received later. The processor 24 is configured to recognize emergency room patients, trauma related patients, and/or patients more likely to have rescanning based on the available data. The clinical finding and/or radiology report 26 are generated with a greater priority for such patients than for other patients.

Referring again to FIG. 2, the interface 27 is a communications port, such as an ethernet card, or another computer network interface. In other embodiments, the interface 27 is a user interface, such as user input device (e.g., keyboard, mouse, trackpad, touchscreen, and/or roller ball). The interface 27 may be a bus, chip, or other hardware for receiving and/or outputting information, such as scan data, clinical indication tag, patient information, clinical finding, scan settings, and/or radiology report 26.

The interface 27 is configured to output the radiology report 26. For example, the radiology report 26 is output to the database 29, the medical imager 22, or a computer. The output from the fulfillment center is a clinical report, which could be automatically sent back to one or several locations such as the electronic health record or electronic medical record system, the referring physician, and/or the patient.

The medical records database 29 is a random-access memory, system memory, cache memory, hard drive, optical media, magnetic media, flash drive, buffer, database, combinations thereof, or other now known or later developed memory device for storing the radiology report 26, patient information, clinical findings, scan settings, clinical indication tag, and/or the deep machine-learned network 25. The medical records database 29 is part of the computer associated with the processor 24 or the medical imager 22 or is a separate or remote database for access over a computer network.

The medical records database 29 or other memory is alternatively or additionally a non-transitory computer readable storage medium storing data representing instructions executable by the programmed processor 24 and/or medical imager 22. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 28 is a monitor, LCD, projector, plasma display, CRT, printer, or other now known or later developed device for displaying the radiology report 26, clinical finding, and/or image of the patient. The display 28 receives the output from the processor 24, database 29, or interface 27. The processor 24 formats the data for display (e.g., mapping to RGB values) and stores the image in a buffer, configuring the display 28. The display 28 uses the image in the buffer to generate an image for viewing. The image includes graphics, alphanumeric text, anatomical scan, and/or other information. The display 28 is at the medical imager 22, the fulfillment center (e.g., processor 24), a physician's computer, or another location.

Since the processor 24 is interconnected with the medical imagers 22, the focus is on generating a radiology report rather than a focus of just generating an image or just reading and reporting given a previously acquired image. The communications allow more than a sequential generation of an image, reading, and reporting. As a result, the radiology report and corresponding clinical findings may be more complete, more accurate, and less likely to lead to other appointments or examinations for the patient.

The use of the deep or other machine-learned network 25 may make the response time of the fulfillment center (e.g., processor 24) more rapid. Due to the application of the network rather than hand programmed series of calculations, the computer operates more quickly to provide a clinical finding and/or radiology report 26.

Figure 4:
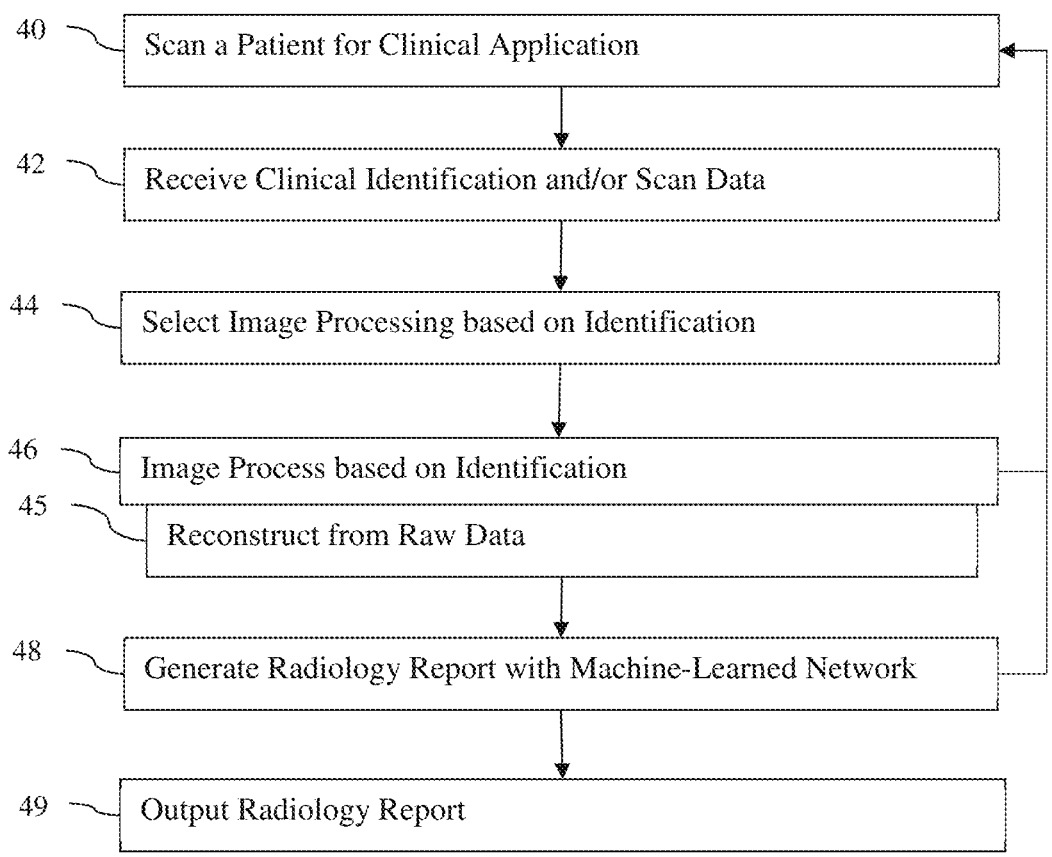
FIG. 4 is a flow chart diagram of an embodiment of a method for imaging and generating a radiology report in a medical system.

FIG. 4 shows one embodiment of a method for imaging a patient and generating a radiology report in a medical system. The imaging, finding, and reporting pieces of the processing chain are linked together so that the final radiology report is more likely complete based on a given examination of the patient and less likely to need a follow-up examination to complete the diagnosis.

The method is implemented by one of the systems of FIGS. 1-3 or another system. For example, the method is implemented by a computer, server, medical imager or other processor. A medical imager scans in act 40 and may rescan in a feedback. An image processor (e.g., server) receives in act 42, selects in act 44, reconstructs in act 45, image processes in act 46, generates in act 48, controls scanning based on feedback to the medical imager, and outputs to a display device in act 49. Different devices may be used.

Additional, different, or fewer acts may be provided. For example, the reconstruction from raw data at the server of act 45 and/or some of the image processing of act 46 is performed instead at the medical imager as part of act 40. As another example, the clinical identification is not received in act 42 or used in act 44. In yet another example, the feedback from act 46 and/or act 48 for controlling the scan of act 40 is not used. Acts for configuring or communicating may be provided.

Acts 44, 45, 46, and/or 48 use one or more hand coded algorithms and/or one or more machine-learned networks. Different learned networks or classifiers are used for each act, but a common network (e.g., multi-task or cascaded network) or a network formed from other networks may be used for implementing one act or combinations of two or more acts. Any type of machine learning and corresponding machine-learned network may be used, such as deep learning with a neural network architecture. Probabilistic boosting tree, support vector machine, Bayesian, or other networks may be used. One or more AI-based algorithms (e.g., machine-learned networks) may be applied for the same task, and a consensus decision (e.g., average) may be included in the final report. For example, the fulfillment center may run several lesion detection algorithms on the same study and report results in a composite manner.

The acts are performed in the order shown (e.g., top to bottom or numerical) or other orders. For example, acts 46 and 45 are performed in a reverse order or simultaneously. Act 45 may be performed before act 44. Act 48 may be performed as part of act 46. Feedback from either of acts 46 or 48 to the scan of act 40 is shown. The resulting repetition may not include act 42 and/or act 45.

In act 40, a medical imaging scanner scans a patient. The medical imaging scanner is any medical imager, such as a CT, MR, nuclear medicine, or ultrasound scanner.

The patient is scanned along a plane or in a volume. Energy, such as x-rays, electromagnetic pulses, acoustic, or other, may be transmitted into the patient. The energy as passed through the patient and detected, and/or a response to the energy is received or detected from the patient. Alternatively, the scan relies on emissions from within the patient, measuring the emissions. The detected response, energy, or emissions are raw scan data.

The raw scan data may be processed as part of the scan. For example, reconstruction is applied. The reconstruction may determine response of the patient by locations within the patient, such as for voxels or pixels in a volume or plane of the patient. For MR, k-space data is reconstructed with a Fourier transform. For CT, projection images from different directions relative to the patient are reconstructed by computed tomography. For nuclear medicine, detected emissions along lines of response are reconstructed by tomography.

Other post-receipt processing may be provided, such as filtering, denoising, segmentation, reformatting, rendering, scan converting, color mapping, and/or amplification. The scan data from any point along this processing path from raw scan data to a rendered, color-mapped image is output by the scan.

The scan uses settings based on an ordered or prescribed type of scan. A physician indicates a clinical application or indication. A technician configures the medical imaging scanner based on the application or indication. Alternatively, the medical imaging scanner uses the application or indication with or without other patient information to self-configure the scan.

The scan data, scan settings, patient information, and/or clinical identification (e.g., application or indication) are passed to a fulfillment center or image processor. A request, a type of scan (e.g., for a different and/or more specific clinical application), or scan parameter settings may be received back from the fulfillment center.

In act 42, the image processor implementing the fulfillment center receives a clinical identification (e.g., application or indication) for the patient. The scan data, patient information, and/or scan settings may be also received. The information is provided over a computer network. Alternatively, the information is received by loading from a memory.

In one embodiment, the image processor and the medical imaging scanner are in different buildings or facilities. For example, the image processor is one or more servers operated by a different entity than a hospital or medical practice operating the medical imaging scanner. The same fulfillment center may be used for multiple medical imaging scanners, such as scanners owned and operated by different hospitals. The same or different types of information are received by the image processor for different medical imaging scanners, such as receiving different clinical identification corresponding to different scans for different patients or reasons and the different scans. Alternatively, the image processor is in a same building or facility as the medical imaging scanner.

The clinical identification may be a symptom or other indication of the reason for the scan. The clinical identification may be an application, such as type of scan. The clinical identification is a label or tag but may be scan settings or other information from which the application or indication may be derived.

In one embodiment, the received scan data is without reconstruction. The image processor is to perform the reconstruction. This may allow the type of reconstruction and/or settings for reconstruction to be responsive to clinical findings or other image processing not available at the medical imaging scanner, at least during the scan. By reconstructing the scan data into a three-dimensional object space based on more information, the reconstruction may result in an image or other scan data more tuned to the clinical need or reporting.

In act 44, the image processor selects imaging processing. Different image processing may be used for different situations. Different settings within a same image process (e.g., different filter kernels) may be used for different situations. Different sets and/or sequences may be used for different situations. Rather than relying on user set configuration, the image processing is selected based on current standards, expert input, and/or other knowledgebase.

The image processor uses the clinical identification to select the image processing. For example, the clinical identification is for a cardiac scan or identifies pain associated with cardiac problems. The selected image processing includes filtering, denoising, stenosis detection, heart wall abnormality detection, severity classification, and/or quantification of heart function (e.g., fractional flow reserve and/or stroke volume). In another example, the clinical identification is a fetal scan or identifies a standard 3-month pregnancy check. The selected image processing includes heartbeat detection, fetus detection, length and/or volume quantification, and/or health classification. The symptom, clinical application, scan settings, other clinical identification, and/or other information are used to select the appropriate image processing.

In act 46, the image processor performs the selected image processing in a selected sequence. The different image processing for the different patients are performed independently. The scan data is image processed based on the selected image processing. Other information may be used in the image processing, such as the clinical identification, scan settings, and/or patient information. The image processing appropriate for the clinical identification is performed.

In one embodiment, the selected imaging processing includes reconstruction. The scan data as received is projection data, k-space data, or line of response data that does not represent specific voxels or locations in the patient. The image processor reconstructs to estimate scalar values for the different locations in the patient from the scan data. Different reconstruction may be performed for different patients and corresponding clinical indications.

Other image processing before or after an initial reconstruction may indicate type and/or settings for reconstruction. The reconstruction may be repeated. For example, a clinical finding indicates a particular type of information may be important, such as heart wall thickness over time. A reconstruction with better or different motion compensation may be used to provide greater resolution, contrast, and/or motion indication for the heart wall. By redoing the reconstruction, the resulting scan data may better represent the information of interest. By using an automated process in the fulfillment center, the better information may be provided without relying on user variance in recognition of the need for different reconstruction.

Other image processing that may be applied includes filtering, denoising, detecting, classification, and/or segmenting from the scan data. Detection may allow detection of anatomy to be used in quantification and/or detection of whether pathology exists in the patient. Filtering and denoising may provide information more directed to the information of interest. Segmenting may be used for quantification.

Another form of image processing may be determining a clinical finding. The clinical finding may include a detection of pathology, location of pathology, and severity. A recommended action and/or comparative information may be included. The clinical finding may be determined with a machine-learned network trained to provide clinical findings, such as from radiology reports, given input scan data, patient information, clinical identification, and/or information (e.g., quantities or detection) from other image processing. In one embodiment, the clinical finding is provided as part of act 48. Alternatively, the clinical finding is performed separately and later used in the generation of the radiology report.

Yet another form of image processing is checking for quality. The scan data may be tested for quality, such as measuring a signal-to-noise ratio, contrast level, and/or resolution. The existence of artifacts, interfering anatomy, and/or other check for quality may be performed.

Based on one or more results of the image processing and/or information generated for the radiology report in act 48, the image processor may feedback information to the medical imaging scanner. The feedback may be a request for repeat of the same scan (e.g., in response to poor quality), a request for a different scan (e.g., in response to a clinical finding), or scan settings for a scan (e.g., in response to a quality check or clinical finding). The feedback allows gathering of better or additional scan data for improving the quality of the eventually generated radiology report.

In response to the feedback, the medical imaging scanner rescans the patient in act 40. The rescanning may be part of a continuation of scanning or restarting scanning. The scan settings and/or request feedback are used to scan the patient. Acts 42, 44, 45, and/or 46 may be repeated for the scan data from the rescan.

The rescan may include scanning of the same part or region of the patient and/or scanning a different part or region of the patient. For example, the same scan (e.g., cardiac scan) is performed again but with one or more different settings (e.g., amplitude). In another example, a first scan is of a liver, while the second scan for rescanning is of another organ based on the information extracted from the liver scan.

In act 48, the image processor generates a radiology report. The scan data, outputs from the image processing (e.g., measured values or quantities), patient information, clinical identification, and/or other information are used to generate the radiology report. Different radiology reports are generated for different patients, such as generating radiology reports for different patients from the different scan data. Even where the same clinical identification is provided for different patients, the differences in pathology reflected in the different scan data and/or patient information result in different radiology reports for the different patients.

One or more clinical findings are generated for the radiology report. The clinical findings may be in the form of free or narrative text. For example, a clause or sentence is generated indicating a pathology, severity of the pathology, and location of the pathology as a summary opinion. A machine-learned network, such as a deep machine-learned text generator, generates the clinical findings of the radiology report. Natural language processing, at least part of which includes a deep machine-learnt network or a machine-learned natural language network, generates the narrative text from the input data. A neural network having been trained from samples of patient radiology reports, scan data, and values for measurements for the patient reports is applied. Different deep machine-learned text generators may be used for different clinical identifications. The clinical identification is used to select the algorithms and/or machine-learned network to generate the radiology report, allowing for training based on a corpus specific to the clinical indication. Alternatively, the text generator is general to different clinical identifications.

The radiology report may be structured. The different information from the image processing is inserted into different fields of the structured report. In other embodiments, the radiology report or part of the report is unstructured. Narrative text is entered.

The radiology report may be generated as part of the linked imaging through reporting system without display of any images for one, more, or all the patients. A human does not view any images from the scan data from after receiving the scan data through the image processing and report generation. A human, such as a technician operating the medical imager may view images during scanning or may not. A human at the fulfillment center may view images and/or other information or may not. The first human to view after sending scan data to the fulfillment center may be a physician viewing the radiology report and any included images.

Where rescanning occurs, the content of the radiology report may be based on the initial scan data and/or the scan data from the rescanning. Clinical findings from the different scan data may be included, such as a general clinical finding based on the initial scan data and a more detailed or specific clinical finding based on scan data from rescanning. One clinical finding may be determined based on scan data from multiple scans.

In act 49, the image processor outputs the radiology report. Different radiology reports are output for different patients and/or medical imaging scanners. The output is to a display, electronic medical records database, referring physician, patient, computer network interface, and/or memory.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for imaging and generating a radiology report in a medical system, the method comprising:
    scanning, by a medical imaging scanner, a patient;
    receiving, by an image processor, a clinical identification of a reason for the scanning for the patient and first scan data from the scanning, the image processor being in a different building than the medical imaging scanner;

selecting image processing for the first scan data from the scanning, the image processing selected based on the clinical identification, wherein the image processing comprises operating on the first scan data after the scanning and wherein the selecting is performed after the scanning to acquire the first scan data;

image processing, by the image processor, the first scan data from the scanning using the selected image processing, the image processing relating the first scan data to scan settings from a clinical finding for pathology generated by the image processing;

feeding back the scan settings to the medical imaging scanner based on the imaging processing, wherein the scan settings are to be used by the medical imaging scanner;

rescanning, by the medical imaging scanner as configured by the scan settings, the patient, the rescanning by the medical imaging scanner different than the scanning due to the configuration by the scan settings;

generating, by a machine-learned network implemented by the image processor, the radiology report in response to the first scan data, the feedback information, and/or second scan data from the rescanning, the radiology report having narrative text characterizing the patient; and outputting the radiology report.

2. The method of claim 1 wherein generating comprises generating with a deep machine-learned text generator as the machine-learned network, and wherein the image processor and the deep machine-learned text generator are in the different building than the medical imaging scanner, wherein the image processor receives the first scan data and clinical identification from the medical imaging scanner, and wherein the image processor performs the selecting.

3. The method of claim 2 wherein scanning comprises scanning with a computed tomography system, a magnetic resonance system, or a nuclear medicine system, and wherein image processing the first scan data comprises receiving the first scan data as projection data, k-space data, or lines of response data and reconstructing to an object space based on the clinical identification.

4. The method of claim 1 wherein image processing comprises filtering, denoising, detecting, classifying, and/or segmenting from the first scan data.

5. The method of claim 1 wherein image processing comprises determining the clinical finding, wherein feeding back the information comprises feeding back the scan settings for the medical imaging scanner, and wherein rescanning comprises rescanning with the scan settings based on the clinical finding.

6. The method of claim 1 wherein generating comprises generating by a machine-learned natural language network.

7. The method of claim 1 wherein image processing comprises determining the clinical finding with a machine-learned network, and wherein generating the clinical report comprises generating the clinical report with the clinical finding and another clinical finding from image processing of the second scan data from the rescanning.

8. The method of claim 1 wherein image processing comprises checking the second data for quality, and wherein feeding back the information comprises feeding back a request to perform the rescanning based on the check of the quality.

9. The method of claim 1 wherein receiving the clinical identification comprises receiving a symptom, and wherein selecting comprises selecting based on the symptom.

10. The method of claim 1 wherein generating the radiology report comprises generating the narrative text including a pathology, severity of the pathology, and location of the pathology.

11. The method of claim 1 wherein outputting comprises outputting to an electronic medical records database, a referring physician, and/or the patient.

12. A system for imaging and generating a radiology report, the system comprising:
a medical imager configured to scan a patient, the configuration being for a clinical application;
a processor configured to receive scan data from the medical imager, then select image processing for the previously received scan data, then apply the image processing to the scan data, then determine a clinical finding from the image processing, the clinical finding being a medical opinion for a type of pathology or disease, then control the medical imager with scan settings based on the clinical finding, the scan settings determined from a relation of the clinical finding to the scan settings, and then generate the radiology report from the clinical finding with a machine-learned network, the processor in a different building than the medical imager; and
an interface configured to output the radiology report.

13. The system of claim 12 wherein the processor is a server at a different facility than the medical imager.

14. The system of claim 12 wherein the processor is configured to apply the image processing as reconstruction, quality assurance of the scan, filtering, denoising, detection, segmentation, classification, quantification, and/or prediction.

15. The system of claim 12 wherein the medical imager is configured to output a clinical identification tag for the clinical application, and wherein the processor is configured to apply the image processing selected based on the clinical identification tag.

16. The system of claim 12 wherein the medical imager is configured to provide the scan data from the scan without reconstruction, and wherein the processor is configured to reconstruct as part of the application of the image processing.

17. The system of claim 12 wherein the interface comprises a computer network interface for output to a medical records database.

18. A method for imaging and generating a radiology report in a medical system, the method comprising:
receiving first and second scan data from first and second medical scanners, the first and second scan data representing first and second patients and being without reconstruction into a three-dimensional object space, the receiving being at a server or workstation in a different location than the first and second medical scanners;
obtaining first and second clinical indication tags for the first and second scan data, the first and second clinical indication tags being first and second, different reasons for scanning of the first and second patients, respectively, to have been performed; then
image processing, including reconstruction, of the first and second scan data by the server or workstation in the different location than the first and second medical scanners, the image processing including the reconstruction of the first scan data different than the reconstruction of the second scan data based on the first and second clinical indication tags for the previously performed scans to acquire the first and second scan data being different, the image processing determining first and second clinical findings for pathologies of the first and second patients, respectively, from the reconstructions of the first and second scan data;

generating first and second radiology reports from information provided by the image processing, the first and second radiology reports including the first and second clinical findings, respectively; and outputting the first and second radiology reports.

19. The method of claim 18 wherein generating comprises generating without display of any images from the first and second scan data to a human after receiving and through the image processing and the generating.

* * * * *